(12) United States Patent
Modavis

(10) Patent No.: US 8,342,403 B2
(45) Date of Patent: Jan. 1, 2013

(54) COMPACT OPTICAL READER SYSTEM

(75) Inventor: Robert Adam Modavis, Painted Post, NY (US)

(73) Assignee: Corning Incorporated, Corning, NY (US)

(*) Notice: Subject to any disclaimer, the term of this patent is extended or adjusted under 35 U.S.C. 154(b) by 178 days.

(21) Appl. No.: 12/907,461

(22) Filed: Oct. 19, 2010

(65) Prior Publication Data

US 2011/0091923 A1    Apr. 21, 2011

Related U.S. Application Data

(60) Provisional application No. 61/253,679, filed on Oct. 21, 2009.

(51) Int. Cl.
*G06K 7/10* (2006.01)

(52) U.S. Cl. ......... 235/454; 235/494

(58) Field of Classification Search .......... 235/454, 235/494, 455; 435/7.1, 287.2
See application file for complete search history.

(56) References Cited

U.S. PATENT DOCUMENTS

| | | | |
|---|---|---|---|
| 7,023,544 B2 | 4/2006 | Cunningham et al. | 356/326 |
| 7,738,047 B2* | 6/2010 | Yelleswarapu et al. | 349/1 |
| 2004/0094058 A1 | 5/2004 | Kasperchik et al. | 101/483 |
| 2005/0070027 A1* | 3/2005 | Gollier et al. | 436/518 |
| 2006/0057707 A1* | 3/2006 | Cunningham et al. | 435/287.1 |
| 2006/0077390 A1* | 4/2006 | Kralik | 356/427 |
| 2007/0154356 A1 | 7/2007 | Modavis | 422/102 |
| 2008/0174860 A1* | 7/2008 | Yelleswarapu et al. | 359/370 |
| 2010/0245694 A1* | 9/2010 | Yelleswarapu et al. | 349/20 |

* cited by examiner

*Primary Examiner* — Thien M Le
(74) *Attorney, Agent, or Firm* — John L. Haack

(57) ABSTRACT

A method and optical reader system for label-independent detection as defined herein. The reader system includes: a launch beam; a first lens; a receptacle for receiving at least one optical biosensor article, the article having a mask on one face, and the mask having at least one aperture there through for receiving and transmitting radiation from the collimated launch beam; an angular separator; and an imager to record the image of the optical biosensor article.

15 Claims, 7 Drawing Sheets

COMPACT OPTICAL READER SYSTEM

CROSS-REFERENCE TO RELATED APPLICATIONS

This application claims the benefit of priority under 35 U.S.C. §119(e) of U.S. Provisional Application Ser. No. 61/253,679 filed on Oct. 21, 2009.

The entire disclosure of any publication, patent, or patent document mentioned herein is incorporated by reference.

BACKGROUND

The disclosure relates generally to an optical reader system and method for optically reading microplates for use, for example, in label-independent detection biosensors, or like applications.

SUMMARY

The disclosure provides a compact optical reader system and a method for optically reading microplates.

BRIEF DESCRIPTION OF THE DRAWING(S)

In embodiments of the disclosure:

DETAILED DESCRIPTION

Figure 1:
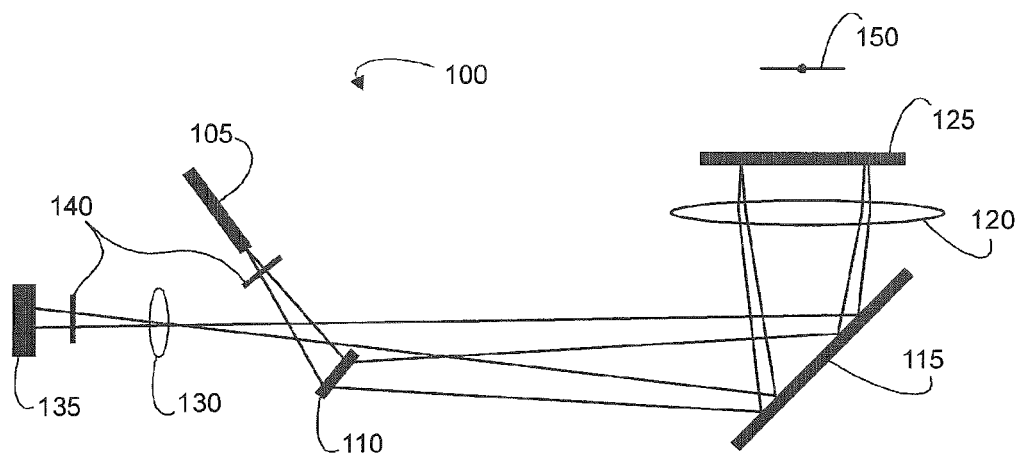
FIG. 1 shows a schematic of a Mod. I system.

Various embodiments of the disclosure will be described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments for the claimed invention.

DEFINITIONS

"Biosensor" or like term refers to an article, that in combination with appropriate apparatus, can detect a desired analyte. A biosensor can combine a biological component with a physicochemical detector component. A biosensor can typically consist of three parts: a biological component or element (such as tissue, microorganism, pathogen, cells, cell component, a receptor, and like entities, or combinations thereof), a detector element (operating in a physicochemical way such as optical, piezoelectric, electrochemical, thermometric, magnetic, or like manner), and a transducer associated with both components. In embodiments, the biosensor can convert a molecular recognition, molecular interaction, molecular stimulation, or like event occurring in a surface bound cell component or cell, such as a protein or receptor, into a detectable and quantifiable signal. A biosensor as used herein can include liquid handling systems which are static, dynamic, or a combination thereof. In embodiments of the disclosure, one or more biosensor can be incorporated into a micro-article.

Commonly owned and assigned copending U.S. Patent Application Publication 2007/0154356 (U.S. Ser. No. 11/436,923) (R. Modavis) discloses at para. [0042] an optically readable microplate having an attached mask with apertures. The mask layer or agent with apertures blocks transmitted light. U.S. Patent Publication 2003/0059855 (Cunningham) discloses a microfilter tray 456, plate tray 458, and incubation assembly bottom portion 602. Neither publication provides for relative motion of a slitted-mask and a biosensor nor a narrow-width slit-biosensor to accomplish enhanced 2D resolution in an optical reader.

"Angular separator," or like terms refers to, for example, a transmission grating, a reflection grating, a prism, or like components, a combination thereof, or a plurality thereof.

Biosensors are useful tools and some exemplary uses and configurations are disclosed, for example, in PCT Application No. PCT/US2006/013539 (Pub. No. WO 2006/108183), published Dec. 10, 2006, to Fang, Y., et al., entitled "Label-Free Biosensors and Cells," and U.S. Pat. No. 7,175,980. Biosensor-based cell assays having penetration depths, detection zones, or sensing volumes have been described, see for example, Fang, Y., et al. "Resonant waveguide grating biosensor for living cell sensing," Biophys. J., 91, 1925-1940 (2006). Microfluidic articles are also useful tools and some exemplary uses, configurations, and methods of manufacture are disclosed, for example, in U.S. Pat. Nos. 6,677,131, and 7,007,709. U.S. Patent Publication 20070141231 and U.S. Pat. No. 7,175,980, disclose a microplate assembly and method. The compositions, articles, and methods of the disclosure are particularly well suited for biosensors based on label-independent detection (LID), such as for example an Epic® system or those based on surface plasmon resonance (SPR). The compositions, articles, and methods of the disclosure are also compatible with Dual Polarized Intereferometry (DPI), which is another type of LID sensor. In embodiments, the biosensor system can comprise, for example, a swept wavelength optical interrogation imaging system for a resonant waveguide grating biosensor, an angular interrogation system for a resonant waveguide grating biosensor, a spatially scanned wavelength interrogation system, surface plasmon resonance system, surface plasmon resonance imaging, or a combination thereof.

A preferred optical system is a constant stare imager. The surface of the biosensor can be, for example, an uncoated surface such as a glass or a plastic, or for example, a coated surface. Suitable surface coating for the biosensor can include, for example, fibronectin, collagen, gelatin, poly-D-lysine, a synthetic polymer, and like coating compositions, and mixtures thereof. The coating composition can be used as a thin film, for example, on certain Epic® biosensor well-plate products commercially available from Corning, Inc. In embodiments, the coating of the coated biosensor can have "reactive groups" and "ionizable groups" and which groups refer to moieties that can chemically react and moieties than can ionize, respectively, and as defined in commonly owned, copending U.S. Ser. No. 12/273,147, filed Nov. 18, 2008, and commonly owned and assigned copending U.S. application Ser. No. 11/973,832, filed Oct. 10, 2007. Another suitable surface coating is disclosed in commonly owned, copending U.S. Ser. No. 11/448,486, filed Jun. 7, 2006. Another suitable surface coating can be, for example, an ethylene-maleic anhydride (EMA) polymer according to T. Pompe (Pompe, et. al, "Functional Films of Maleic Anhydride Copolymers under Physiological Conditions," *Macromol. Biosci.*, 2005, 5, 890-895). The polymer can be, for example, a polyacrylic acid polymer, or copolymer containing acrylic acid monomers. The polymer can be, for example, a carboxylated polysaccharide or like materials as disclosed, for example, in U.S. Pat. Nos. 5,242,828 and 5,436,161.

"Include," "includes," or like terms means encompassing but not limited to, that is, inclusive and not exclusive.

"About" modifying, for example, the quantity, dimension, process temperature, process time, and like values, and ranges thereof, employed in describing the embodiments of the disclosure, refers to variation in the numerical quantity that can occur, for example: through typical measuring and handling procedures used; through inadvertent error in these procedures; through differences in the manufacture, source, or quality of components and like considerations. The term "about" also encompasses amounts that differ due to aging of or environmental effects on components. The claims appended hereto include equivalents of these "about" quantities.

"Consisting essentially of" in embodiments refers, for example, to optical readers and associated components, to an assay, to method of using the assay to screen compounds, and to articles, devices, or any apparatus of the disclosure, and can include the components or steps listed in the claim, plus other components or steps that do not materially affect the basic and novel properties of the articles, apparatus, or methods of making and use of the disclosure, such as particular components, a particular light source or wavelength, a particular surface modifier or condition, or like structure, material, or process variable selected. Items that may materially affect the basic properties of the components or steps of the disclosure or that may impart undesirable characteristics to aspects of the disclosure include, for example, having for example, moving parts which can contribute motion, noise, wear, and unnecessary complexity and expense to the reader system.

"Optional," "optionally," or like terms refer to the subsequently described event or circumstance can or cannot occur, and that the description includes instances where the event or circumstance occurs and instances where it does not. For example, the phrase "optional component" or like phrase means that the component can or can not be present and that the disclosure includes both embodiments including and excluding the component.

The indefinite article "a" or "an" and its corresponding definite article "the" as used herein means at least one, or one or more, unless specified otherwise.

Abbreviations, which are well known to one of ordinary skill in the art, may be used (e.g., "h" or "hr" for hour or hours, "g" or "gm" for gram(s), "mL" for milliliters, and "rt" for room temperature, "nm" for nanometers, and like abbreviations).

Specific and preferred values disclosed for components, times, operations, and like aspects, and ranges thereof, are for illustration only; they do not exclude other defined values or other values within defined ranges. The article, apparatus, and methods of the disclosure include those having any value or any combination of the values, specific values, more specific values, and preferred values described herein.

In embodiments of the disclosure, the issue of providing a high resolution optical reader having, for example, a small footprint, such as about 12 inches by 12 inches, and small total volume such as about 12 inches by 12 inches by 12 inches, can be overcome by, for example, eliminating certain complex subsystems, such as individual well plate scanning capability, and removing and replacing with less complex subsystems, for example, a whole-plate imager that can simultaneously record all wells of the well plate in a single image and free-of (i.e., without) moving parts.

In embodiments, the disclosure provides two optical reader (OR) systems for use, for example, in label-free detection: a Modification I Optical Reader (Mod. I) and a Modification II Optical Reader (Mod. II). A primary difference between the Mod. I and the Mod. II configurations is the relative placement of a transmission grating. One salient advantage of the Mod. I system is that the system's sensitivity can be tuned to the dispersion relation of the resonant sensor. One salient advantage of the Mod. II system is that it has superior spatial resolution. The Mod. II system has been demonstrated to have comparable performance on cell and biochemical assays compared to a commercially available SLID-based Epic® instrument. Details of analysis routines are provided including a summary of the performance of the readers regarding, for example, noise floor and the use of the readers in cell and biochemical assays.

In embodiments, the disclosure provides an optical reader system comprising:

a launch beam;

a first lens;

a receptacle for receiving at least one optical biosensor article, the article having a mask on one face, and the mask having at least one aperture there through for receiving and transmitting radiation from the collimated launch beam;

an angular separator, i.e., a transmission grating; and an imager to record the image of the optical biosensor article, the first lens collimates the launch beam and also concentrates the transmitted radiation from the biosensor article, the angular separator being situated before the receptacle and between the launch beam and the first lens, such as in the Mod. I configuration, or after the receptacle and between the first lens and the imager, such as in the Mod. II configuration.

Interrogation of a commercially available well plate, such as an Epic® microplate, results in the desirable resonant light combined with unwanted specular and background light from the sensor itself. To maximize the dynamic range of the detection system two linear polarizers can optionally be used: one polarizer can be situated on the launch-side (input polarizer) and one polarizer can be situated on the receive-side of the microplate (output polarizer). Selecting optimum angles for these polarizers can provide enhanced dynamic range resulting in improved signal-to-noise since unwanted specular and background light are minimized. In general, the angle between these two polarizers is other than 90 degrees (i.e., not 90)°. This optimized linear polarizer condition also provides an improvement in the crosstalk performance of the disclosed optical reader system. The dynamic range can be increased by from about 2 to about 10 times, which in turn provides an increase in the signal-to-noise ratio by from about the square root of 2 to about the square root of 10. The cross-talk of the optical reader system is reduced by from about 2 to about 10 times as a result of the reduction in the broad slowly spectrally varying background. An "imager" generally refers to any suitable imaging device that can capture or record an image from an irradiated well plate in the disclosed optical reader system including for example, a digital camera, a CCD image sensor, a CMOS image sensor, and like devices.

In embodiments, the transmissive grating can provide, for example, from about 100 to about 3,000 lines per millimeter, from about 150 to about 2,500 lines per millimeter, from about 200 to about 2,000 lines per millimeter, and like lines per millimeter, including intermediate values and ranges. The transmission gratings were from Wasatch Photonics (http://www.wasatchphotonics.com), such as part numbers: 1006-2, 1002-2, and 1008-1. Substitutes or equivalents of transmission gratings are, for example, reflection gratings, or a prism or series of prisms. Any optical element that can angularly separate (i.e., an angular separator) the spectrum of a source can be used. For gratings, this angular separation is given by:

$$d*(\sin\theta + \sin\phi) = m\lambda$$

where d is the spacing between the lines, $\theta$ is the angle of incidence, $\phi$ is the angle of the exiting light with respect to the grating, $\lambda$, is the wavelength, and m is the grating order.

In embodiments, the reader system can further comprise at least one optical biosensor article situated in the receptacle. The optical biosensor article can comprise, for example: a radiation permeable base having a first face and a second face; a liquid-tight well-plate on the first face; and a mask on the second face, the mask having at least one radiation permeable aperture. A suitable well plate having a biosensor for use with the optical reader system of the disclosure can include, for example, an optically readable microplate, as disclosed in commonly owned and assigned, copending application U.S. Ser. No. 11/436,923, patent application publication no. 2007/0154356.

In the abovementioned Mod. I system the plane of the virtual object image of the optical biosensor article can be situated beyond the area or plane occupied by the optical biosensor article and collimating lens by, for example, from about 100 to about 200 millimeters.

The angular separator can be, for example, at least one of a transmission grating, a reflection grating, a prism, and like articles or devices, a combination thereof, or a plurality thereof. In embodiments, the angular separator can be, for example, a transmission grating situated between the launch fiber and the first lens (Mod. I), i.e., after the launch fiber and before first collimating lens with respect to radiation propagating from the launch beam.

In embodiments, the angular separator can be a transmission grating situated between the first collimating lens and the imager (Mod. II), i.e., after the first collimating lens and before the camera. "Between" when used in the context of the disclosed optical reader system refers the relative placement or ordering of system components with respect to the radiation path and not necessarily the spatial ordering of system components.

The Mod. I system or Mod. II system configurations can optionally further include, for example:
  a fold mirror situated between the transmission grating and the first collimating lens;
  a second imaging lens situated between the first collimating lens and the camera;
  at least one polarizer situated near the launch beam, near the imager or camera, or a combination thereof;
  or a combination of the foregoing alternatives.

In embodiments, the launch beam can be, for example, a super luminescent diode (SLD) coupled to single-mode fiber.

In embodiments, the disclosure provides a method for label-independent detection comprising:
  providing the label-independent detection system comprising an optical reader system comprising:
    a launch beam;
    a transmission grating;
    a first collimating lens;
    an optical biosensor article having at least one liquid in at least one fluid-tight well, the article having a mask on one face, and the mask having at least one aperture therethrough for receiving and transmitting radiation from the launch beam;
    a receptacle for receiving the optical biosensor article; and
    an imager to record the well-plate image; and
  recording and interpreting the recorded image or pseudo quasi-image attributable to the smear of the image in the dispersive direction.

The imaging can be accomplished with the disclosed optical reader system which, in embodiments, can be characterized as being "constant stare" reader.

Interpreting the image can comprise, for example, comparing the location or centroid of the signal region image to the location or centroid of the reference region image for a well. The masked microplate can include a base comprised of, for example, a glass, a polymer, a composite, or like materials, a combination thereof. The masked microplate can be a well-plate comprised of, for example, at least one well for liquid, and the mask comprises a radiation opaque layer. The mask having appropriately situated aperture(s) the can be formed by any suitable method, for example, photolithography, contact printing, or like methods that employ a photomask in direct contact with a substrate coated with an imaging photoresist layer. Another suitable method includes, for example, a cast and cure process, such as with a selectively deposited UV curable film or printed ink.

The aperture can be any suitable geometry and multiplicity, such as at least one of a circle, an oval, a square, an elongate rectangle, a parallelogram, a rhombus, a trapezoid, a triangle, and like shapes, or combinations thereof, or multiples thereof.

In embodiments, the aperture can comprise at least one slit. The masked aperture can comprise, for example, a plurality of slits, such as from one edge to another edge of the base, or intermediate lengths or segments thereof; for example, horizontal slits, vertical slits, diagonal slits, cross-hatched slits, or a combination thereof. The slit or slits can be, for example, situated on the base to intersect at least a portion of the projection of one or more well regions on the base. The slit can have a width of from about 10 to about 1,000 micrometers, from about 50 to about 500 micrometers, from about 100 to about 400 micrometers, from about 150 to about 300 micrometers, and like slit widths, including intermediate values and ranges.

The aperture can be, for example, at least two un-masked areas within the area defined by the projection of a well region through the base. The aperture can be, for example, a pair of un-masked areas for each well of the well plate, the pair of un-masked areas can be, for example, two co-linear elongate rectangles aligned or situated end-to-end, a first elongate rectangle being the signal region, and the second elongate rectangle being the reference region. In operation the aperture(s) can admit radiation from a source through the mask, and permit the radiation to contact the second face of the base and to transmit the radiation to at least one well of the optionally fluid-tight well-plate on the first face. The first elongate rectangle and the second elongate rectangle can have, for example, a width of from about 10 to about 1,000 micrometers, from about 20 to about 500 micrometers, from about 30 to about 400 micrometers, from about 50 to about 300 micrometers, and like widths, including intermediate values and ranges. The first elongate rectangle and the second elongate rectangle can have, for example, a length of from about 10 to about 2,000 micrometers, from about 20 to about 1,500 micrometers, from about 30 to about 1,000 micrometers, from about 50 to about 500 micrometers, and like lengths, including intermediate values and ranges.

In embodiments, the masked aperture or slitted-mask can be, for example, as disclosed in commonly owned and assigned copending application U.S. Ser. No. 61/253,692 (filed concurrently herewith)(SP09-283P) entitled "OPTICAL READER HAVING ENHANCED TWO-DIMENSIONAL RESOLUTION." Briefly, in embodiments, the slitted-mask can be a moveable stationary slit that can conceal substantially the entire well and the biosensor with the exception of a narrow slit or aperture region in the mask that reveals the sensor region, the reference region, or both. The slitted-masked grating sensor can have the narrow diagonal slit and the slit can have a slit-width of, for example, about 200 micrometers. The orientation of the slit can be vertical, horizontal, diagonal, and intermediate orientations with respect to an edge of the mask or an edge of the sensor. Preferably the slit orientation is not parallel to the dispersive direction as determined by the angular separator (e.g., the transmission grating). In embodiments, an alternative to the moveable slitted-mask is a grating sensor "slice" or "sliver" configuration having minimized biosensor surface area which minimizes the signal area and optional reference area of the biosensor. In embodiments, the minimized biosensor surface area can be advantaged by, for example, limiting the amount of precious target (e.g., protein) or precious ligand that is needed or consumed in target immobilization and ligand binding studies. In embodiments, the slit-mask can be prepared with a thin sheet of plastic, metal, or like materials, having one or more narrow (e.g., 200 micrometers wide) slits. When the size of the biosensor is limited in one dimension (to perform a similar function as the slit), the microplates can be made in the same manner as a commercial plate except that the master (press plate) can have a sensor pattern of the reduced size.

In embodiments, the disclosure provides a label-independent detection system comprising: the abovementioned optical reader systems and as described herein.

Optical Reader System—Modification I (Mod. I)

Referring to the Figures, a Mod. I system (100) is shown in FIG. 1. A super luminescent diode (SLD) coupled to single-mode fiber (105) serves as the launch beam. This expanding beam passes through a transmission grating (110) and is deflected towards the fold mirror (115). The beam is then collimated by a large collimating lens (120) in close proximity to a microplate (125). This collimated beam impinges on the microplate at a small (wavelength dependent) angle of incidence and is reflected back towards the collimating lens. This reflected light is then concentrated by the collimating lens. At a point where the reflected beam size is minimized an optional imaging lens (130) is situated, which forms an image on a CCD camera (135). The optional second, separate camera lens (130) can further manipulate the light from the microplate. The second lens (130) is optional in the configuration of FIG. 1 since the collimating lens, in principle, can accomplish both purposes.

In the Mod. I configuration the imaging lens (130) can be positioned such that the virtual object plane (150), to be imaged on the camera sensor, is located at either a selected distance in front of the microplate, or alternatively, at a selected distance behind the microplate. In embodiments, it may be preferable to place the virtual object plane (150), behind the microplate to minimize any deleterious effects that local variations in the bow, flatness, or both, of the microplate may have on the image quality. In a conventional imaging system, the amount of defocus that a real object can tolerate is very small. However, in the Mod. I system the depth-of-focus can be very large because only collimated light is reflected by the object. The local deviations from microplate flatness can cause the image of the virtual object to be distorted for virtual object planes in front of or behind the microplate. These distortions can be greater for virtual object planes in front of the microplate since the overall beam is converging and therefore the virtual object size is smaller than the actual object. This can result in distortions from the non-flat microplate having a greater impact in relation to the size of a virtual object than for the virtual object located behind the actual microplate.

Since the angle of incidence on the microplate is wavelength dependent, as a result of the dispersive character of the transmission grating, the lateral location of the chosen virtual object plane away from the actual microplate is wavelength dependent. Any change in the wavelength of a biosensor on the microplate, such as occurs during a biochemical event, results in a shift of the lateral location of the virtual object. This shift in the position of the virtual object can be detected by the camera and signals the magnitude of any change within each well.

The image that is formed on the camera's CCD sensor consists of spatial information about the well geometry in the direction that is perpendicular to the dispersive direction of the transmission grating. The other direction (dispersive direction) is a convolution of the spatial information of a well with the spectral resonance of that well. Thus, spatial information can be retained in one direction while in the dispersive direction spatial information can be "mixed" with the spectral resonance of the well. Since the Mod. I system images a virtual object, the spatial information in both dimensions can be partially obscured by Fresnel diffraction.

Two shortcomings of Mod. I system relative to the Mod. II system include, for example, the aforementioned Fresnel diffraction obscuration, and difficulty in obtaining a small dispersion imaged on the camera in wavelength per pixel. With a 1,200 lines/mm transmission grating, this system yielded a dispersion of about 400 pm/pixel. Thus, detection of shifts as small as about $1/400$ pixel may be needed for 1 pm (picometer) spectral resolution. More favorable dispersions (i.e., lower pm/pixel values) are achievable with the Mod. II system, even with transmission gratings having fewer lines/mm.

A significant advantage of the disclosed Mod. I system over other spectrographic systems, (e.g., SLID, i.e., Scanning Label Independent Detection; and a swept wavelength system as described in U.S. Pat. No. 7,576,333 (Corning patent), is that the angle of incidence is wavelength dependent. This enables the sensitivity to be optimized such that small changes in the resonant wavelength will create large changes in the angle of the reflected light. This sensitivity enhancement cannot be accomplished in spectrographic systems that use a fixed angle of incidence. When the transmission grating (110) was placed after the microplate (125), the above mentioned Mod. I system shortcomings were both eliminated.

Optical Reader System—Modification II (Mod. II)

Figure 2:
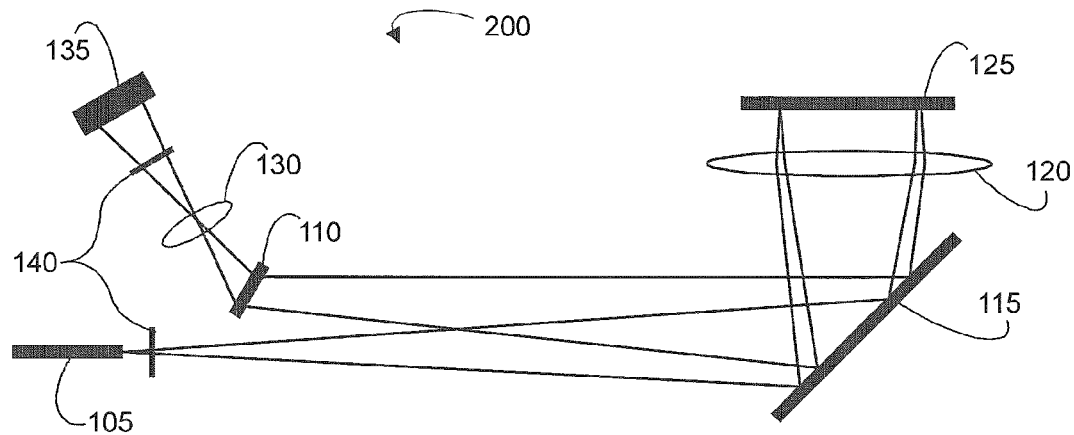
FIG. 2 shows a schematic of a Mod. II system.

The Mod. II system (200) is illustrated in FIG. 2. This system is similar to the Mod. I configuration except that the transmission grating (110) is instead located after the collimating lens (120) and ahead of the camera (135) and its imaging lens (130) as shown in FIG. 2.

Another difference is that the imaging lens (130) is positioned such that the microplate (125) and CCD camera sensor (135) are an object-image pair. Since the actual microplate is imaged, the spatial information is preserved (to within the resolution limits of the lens) in the direction perpendicular to the dispersive direction of the transmission lens. As with the Mod. I system, the spatial information in the dispersive direction of the transmission grating can be convolved with the spectral resonance shape of the well.

Figure 3:
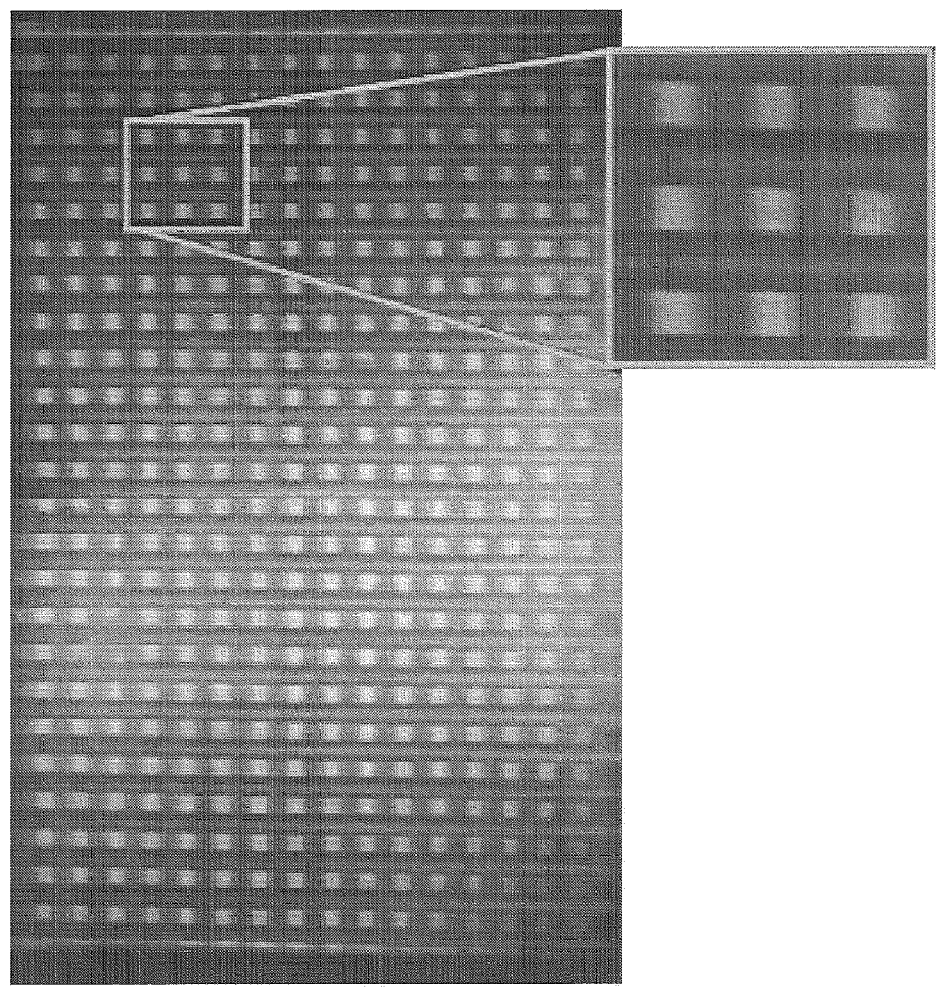
FIG. 3 shows an exemplary full plate image and a magnified region (inset) image from the Mod. II system.
Figure 4:
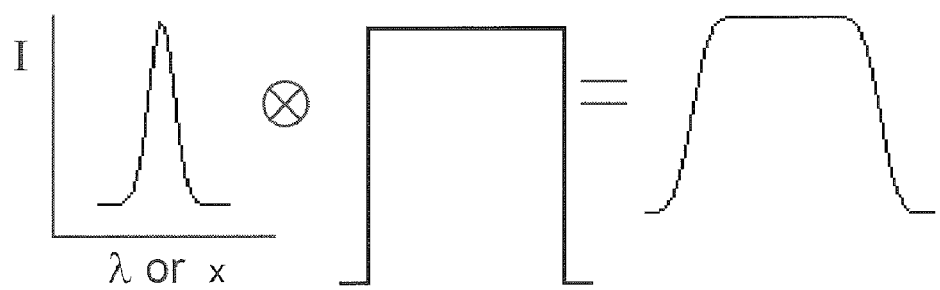
FIG. 4 shows an exemplary detected intensity profile in which the spectral resonance is convolved with the well dimension.

An example image from a Mod. II system is shown in FIG. 3. The full plate image is left and a magnified region (inset) is right. The wells appear very sharp in the vertical direction, i.e., perpendicular to the dispersion of the transmission grating, while the convolved spectral and spatial information (inset) appear "smeared" in the horizontal direction. FIG. 4 graphically illustrates how the resonance shape is convolved with the extent of the well, i.e., converted from wavelength space to the appropriate spatial coordinate. The shape of the spectral resonance (converted to coordinate space) is convolved with the well dimension to yield the detected intensity profile in the dispersive direction where $\lambda$ is wavelength and x is distance along the dispersive direction.

In embodiments, an optional enhancement to either the Mod. I or the Mod. II configurations can be, for example, the addition of an optional polarizer (140) (input polarizer) on the launch side (105) and another polarizer (140) (analyzer) (output polarizer) on the receive side (135) of the layout as optionally shown in both FIGS. 1 and 2. The orientation of these polarizers can be selected to maximize the contrast seen in the image. Increasing the contrast of the image also reduces the crosstalk between adjacent wells. Suitable polarizers include, for example, Polarcor™ Wide Band Glass Polarizers available from Corning Incorporated.

Data Analysis

Three aspects of the data analysis for the disclosed optical reader systems include: wavelength calibration; well searching routine; and the centroid routine.

Wavelength Calibration

To consistently record the wavelength shifts that can occur between an initial and subsequent read of the microplate, each well of the microplate can be calibrated. The calibration procedure replaces the microplate with a calibration plate having a flat mirror-like surface instead of the microplate with biosensors. The broad spectral width of the super luminescence diode (SLD) (105) can be replaced with a tunable laser. By monitoring the location of the imaged wells as the wavelength of the laser is tuned, a calibration based on wavelength/pixel can be obtained. Measurements of pixel shift on the imager or camera for a given well can then be readily converted into wavelength shift.

Well Searching Routine

In the disclosed optical reader systems, the image of the microplate contains spatial information in one direction and a combination of spectral and spatial information in the perpendicular, dispersive direction. Since the resonance wavelength can vary from well-to-well and from microplate-to-microplate, the location of each well in the image can vary from microplate-to-microplate and from well-to-well. For this reason, a routine was devised to automatically find the center of each well during the initial microplate read. Subsequent readings of the microplate use the well centers derived from the initial read. This well finding routine can accommodate a variety of well spacings and placements, including "dead-well" recognition, and can be accomplished by manual or automated implementations.

In embodiments, a suitable well finding routine can be, for example:
1) obtain a grey scale image from the imager (camera);
2) perform a convolution of the image with a suitable function (e.g., Gaussian); and
3) find the location of all the peaks in intensity in the resulting convolved image (these locations correspond to the center of each well).

Centroid Routine Description

For each read of the microplate, the wavelength of each region of interest (signal region, reference region, or the entire well) can be determined. Although the dispersive direction contains both spatial and spectral information, the dispersive direction is treated in the same manner as the spectral information in the commercially available Corning Epic® system. The method operates on waveform measured in the dispersive direction for each region of interest. This waveform is illustrated on the right side of FIG. 4. The center wavelength is found by calculating the centroid of this waveform considering only those points above a prescribed threshold.

The steps for the determining the centroid wavelength for a given well can include, for example:
1) defining a window for a column (or columns) of pixels, the center of this window is based on the center location found in the above mentioned well finding routine;
2) finding the average value of the intensity of two points, one at each edge of the window;
3) normalizing the waveform such that the maximum value is 1 and the value determined in step 2) is zero;
4) oversampling the waveform by inserting n intensity points equally spaced between each measured point (using linear interpolation), where n can be, for example, from about 0 to about 20;
5) convolving the data with a Gaussian having a width of, for example, about 3 to 8 pixels (The width can vary, for example, from about 0.05 to about 40 pixels);
6) eliminating all points that are below the threshold value. The threshold value is typically from about 0.25 but can vary from about 0.02 to about 0.98; 7) subtracting 0.25 from each point;
8) calculating the centroid pixel value (i.e., a center of mass calculation); and
9) converting the centroid pixel value to wavelength using the data obtained in the calibration routine.

EXAMPLES

The following examples serve to more fully describe the manner of using the above-described disclosure, as well as to set forth the best modes contemplated for carrying out various aspects of the disclosure. It is understood that these examples do not limit the scope of this disclosure, but rather are presented for illustrative purposes. The working examples further describe how to make and use the articles and methods of the disclosure.

The following sections summarize the experimental results for the Mod. II system with respect to noise performance and in cell assay and biochemical assay performance.

Example 1

Figure 5:
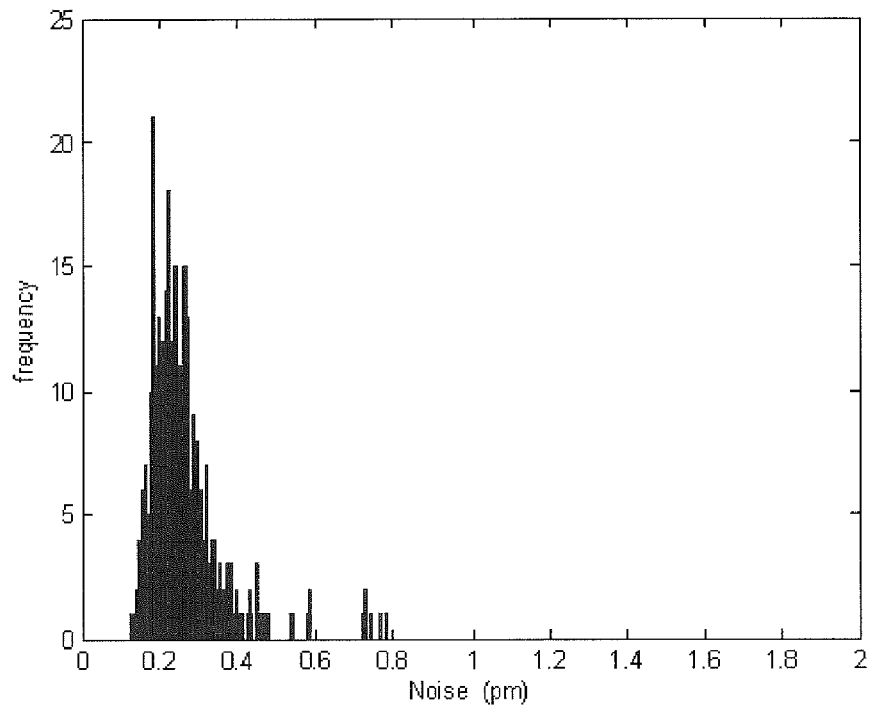
FIG. 5 illustrates an unreferenced noise histogram for the Mod. II system.

Noise measurements The Mod. II system noise was characterized by taking twenty (20) measurements each having a ten (10) second duration. The standard deviation (one sigma) of the wavelength (centroid) value was computed and this represents the noise of the measurement. Two types of noise were computed: unreferenced and referenced. Unreferenced noise consists of the noise for an 800 micron wide region of the well. An unreferenced noise histogram of this noise is shown in FIG. 5, having a median value of 0.24 picometers (pm).

Figure 6:
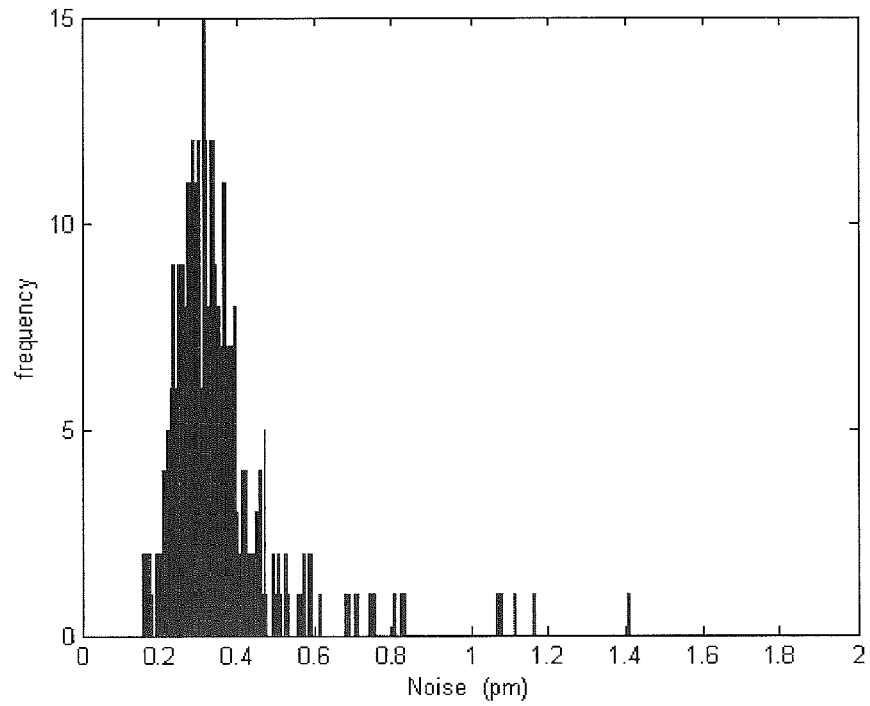
FIG. 6 illustrates a referenced noise histogram for the Mod. II system.

Referenced noise consists of the noise associated with the difference between two separated 800 micron wide regions in each well. FIG. 6 illustrates a referenced noise histogram for the Mod. II system. The standard deviation of this difference for twenty measurements (ten seconds each) is shown in FIG. 6. Here the noise is 0.32 pm. The referenced noise is notably almost exactly the square root of two ($\sqrt{2}$) times larger than the unreferenced noise, which is consistent with the noise arising from a random process.

Example 2

Figure 7:
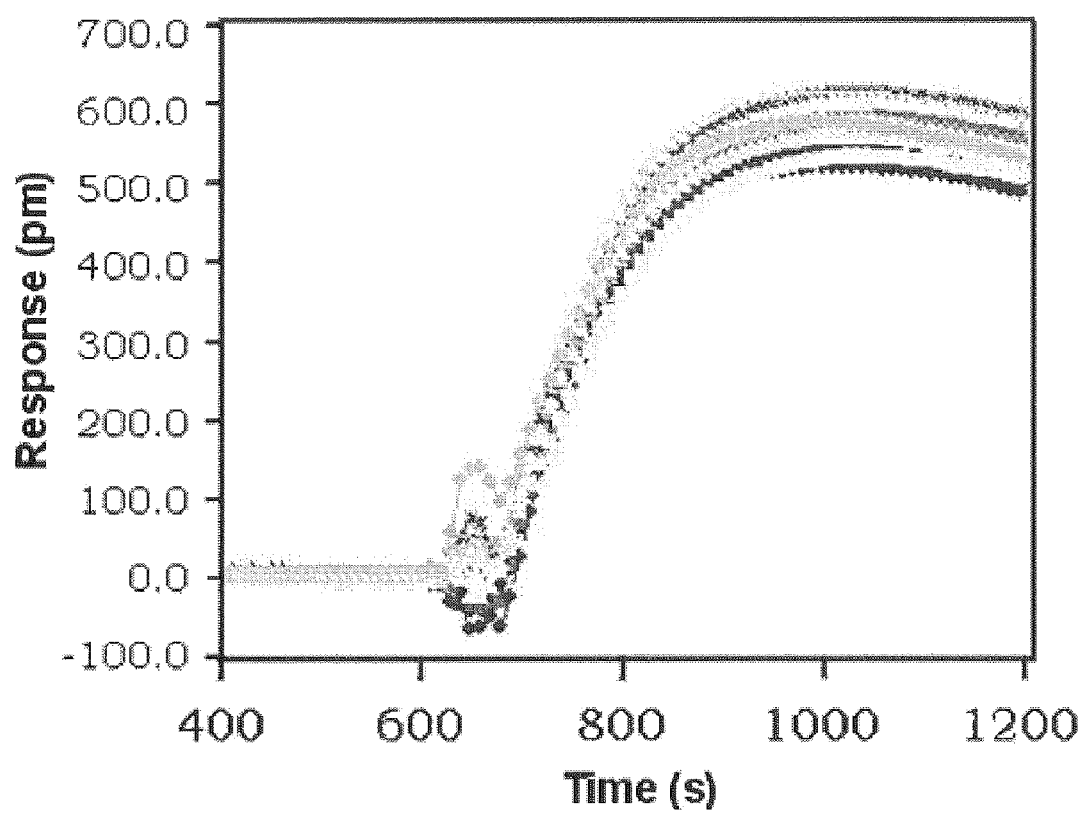
FIG. 7 shows HEK293/SFFLR cell assay results for one column of positive controls.

Cell assay results An HEK293/SFFLR cell assay was run on the Mod. II system. The full microplate was used with a series of positive and negative control wells. The response of the positive control wells is shown in FIG. 7. The baseline read lasted up until about t=600 seconds at which point a candidate compound was added to the well-plate. An advantage of the disclosed Mod. II system compared to the commercially available Epic® system, is that the assay response can be monitored during and immediately after compound addition. The true response at the moment of compound addition is somewhat obscured by the turbulence induced by pipetting. Another advantage is that the measurement time for each data point can be about 10 seconds compared to about one minute for the Epic® system. The measurement time can be increased, for example, up to one measurement every 60 ms with an increase in the noise level of the system.

The performance of this assay is characterized by a Z'=0.80; similar performance can be obtained with the Epic® system. The positive controls had a mean and standard deviation of 569 pm and 29 pm, respectively. The negative controls had a mean and standard deviation of 1 pm and 10 pm, respectively. FIG. 7 shows HEK293/SFFLR cell assay results for one column of positive controls.

Example 3

Biochemical assay results The success of the cell assay mentioned above with the Mod. II system prompted an investigation of this method for biochemical assays. Biochemical assays usually require greater sensitivity than cell assays because of their much smaller signal levels. The initial biochemical assay run on this platform was the standard biotin/streptavidin (B/SV) assay. This assay generally yields signal levels of about 50 pm with a Z' greater than 0.5. The initial results showed an average signal level of about 50 pm. However, the variability among the positive and negative control wells was very high resulting in a poor Z' value of less than zero.

An experimental investigation determined the cause of this high variability. It was first noted that very small perturbations to the microplate, such as adding a small weight to the plate, would cause a large splay in the signal values among the wells. This suggested that an interferometric effect may be responsible. A series of experiments showed that the microplate was the source of this variability and not the optics of the Mod. II system.

Figure 8:
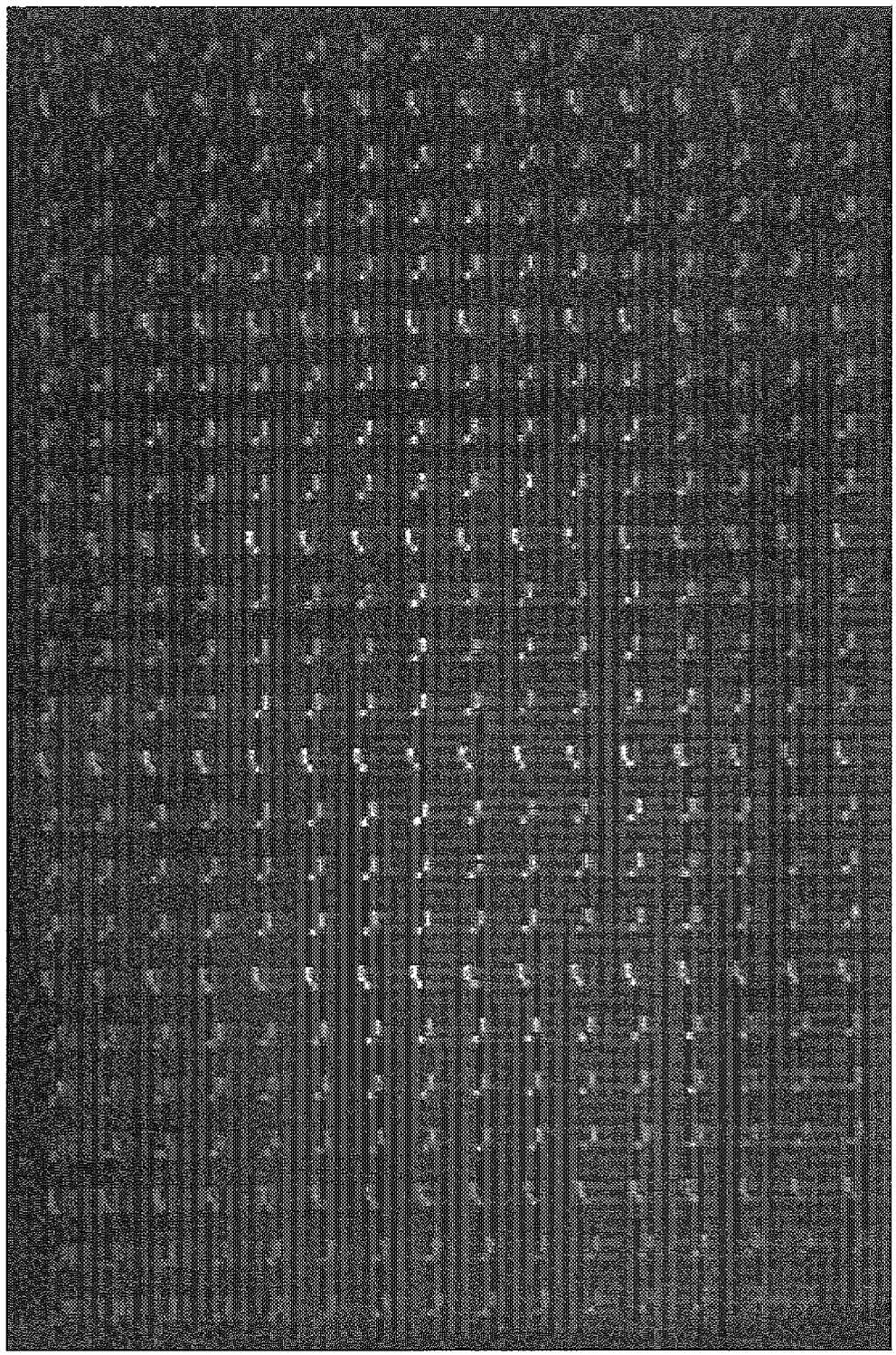
FIG. 8 shows an exemplary image obtained from a microplate having a 200 micrometers slit-mask across each row of wells of the microplate.

A solution to the variability problem was experimentally investigated. The solution consisted of restricting the aperture of each 2 mm×2 mm biosensor well with a mask having a narrow slit. The width of the slit was, for example, about 200 microns and oriented in the dispersive direction and the length extended the full 2 mm of the biosensor well. FIG. 8 shows an exemplary appearance image when using this mask with a biochemical microplate having a 200 micron slit mask across each well. In FIG. 8 there are two distinct regions in each well separated by a distance in the dispersive direction which corresponds to the wavelength difference between the two regions.

Figure 9:
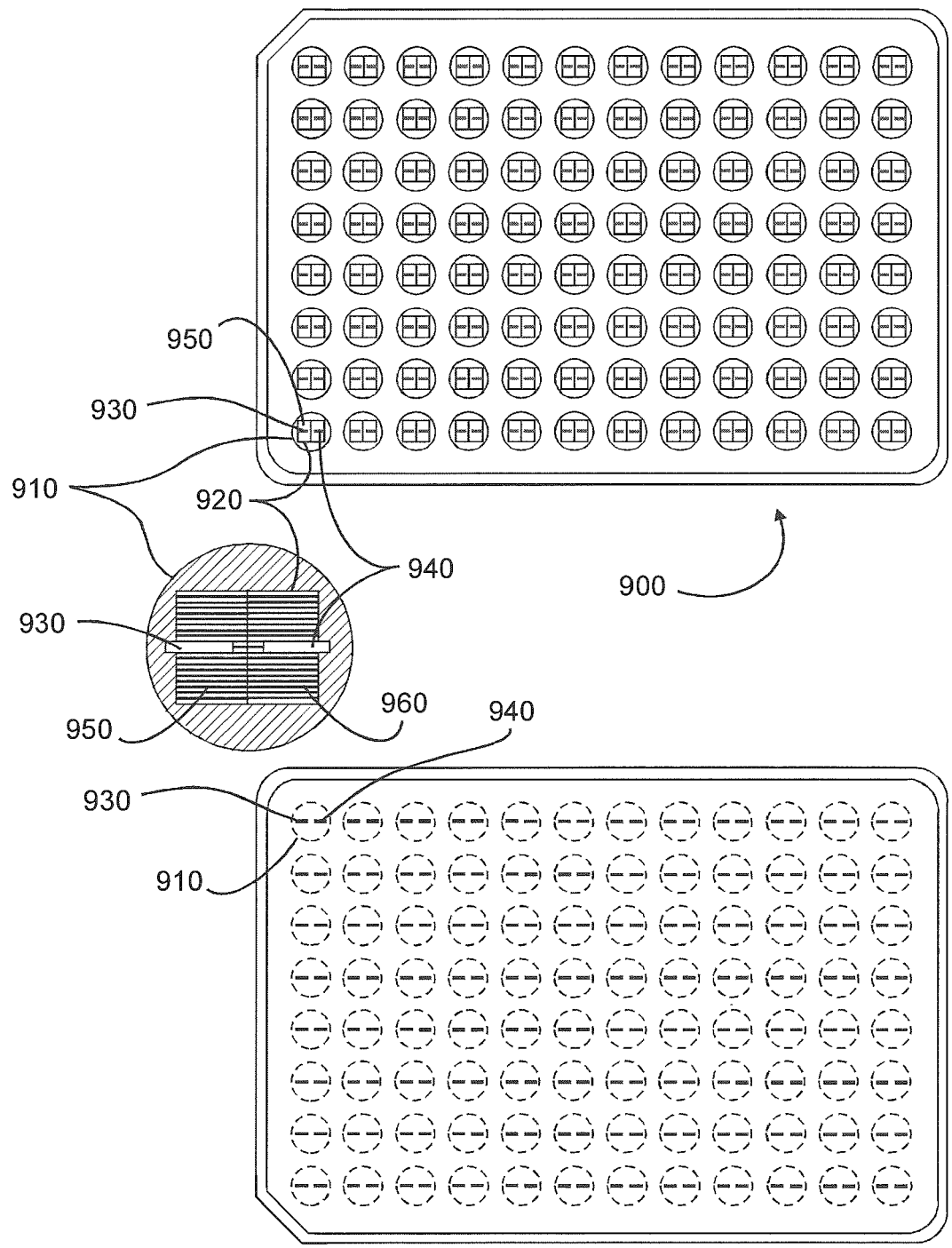
FIG. 9 shows top and bottom views of a masked well plate.

Referring to FIG. 9, within a biochemical microplate (900), each well (910) having resonant grating (920), can be divided into a signal region (930), and a reference region (940), each region typically having different resonant wavelengths.

Figure 10:
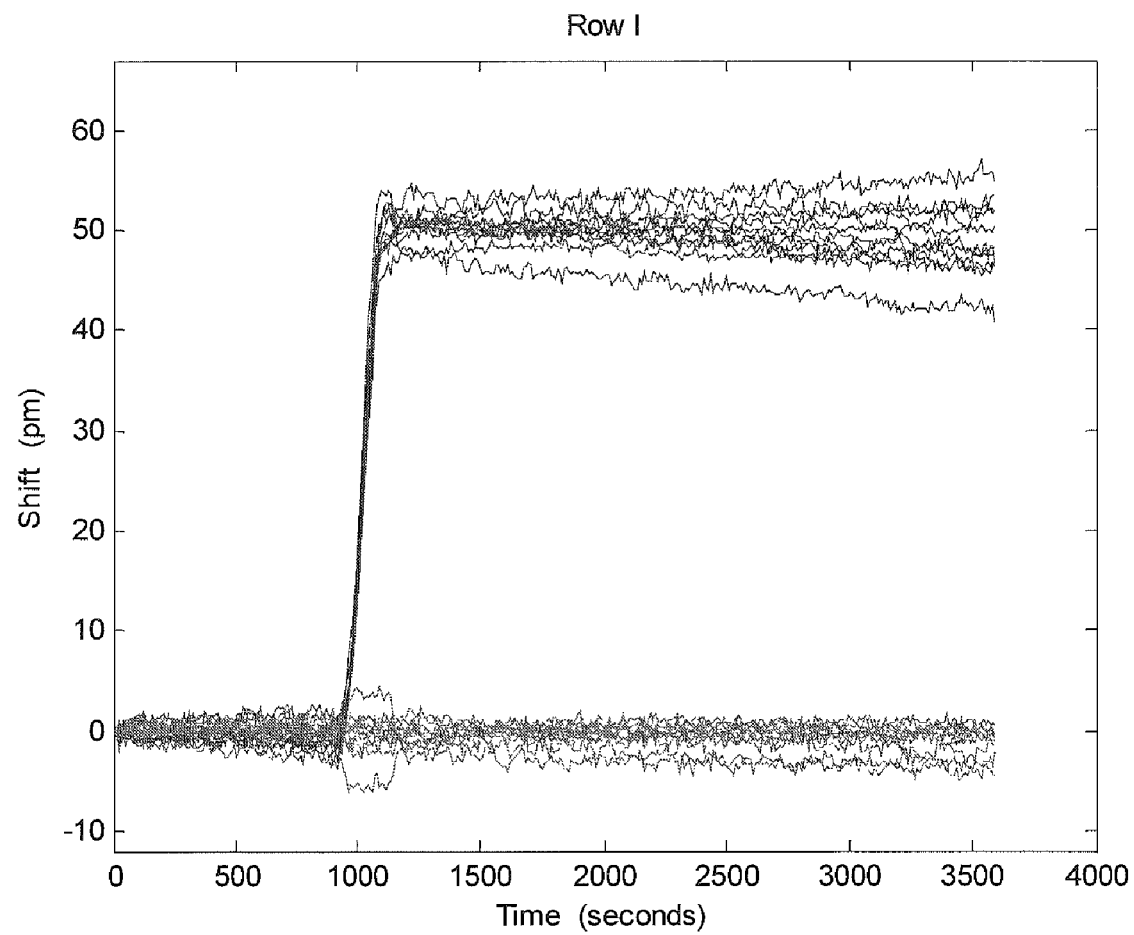
FIG. 10 shows exemplary biochemical assay results for positive and negative controls for a single row of a microplate.

FIG. 10 shows biochemical assay results for positive controls (upper traces) and negative controls (lower baseline traces) for row 1 of a masked microplate. A biotin/streptavidin (B/Sv) assay was performed using the slit mask. The variability for both positive and negative controls was very low and provided a Z' of 0.83. Several biochemical assays have been accomplished on the Mod. II system, and a commercial Epic® instrument. In all instances, the performance of the Mod. II system was comparable to a commercial Epic® instrument.

The disclosure has been described with reference to various specific embodiments and techniques. However, it should be understood that many variations and modifications are possible while remaining within the spirit and scope of the disclosure.

What is claimed:

1. An optical reader system comprising:
   a launch beam;
   a first lens;
   a receptacle for receiving at least one optical biosensor article, the optical biosensor article having: a radiation permeable base having a first face and a second face; a fluid-tight well-plate on the first face; and a mask on or adjacent to the second face, and the mask having at least one aperture therethrough for receiving radiation from the collimated launch beam and transmitting radiation from the biosensor article;
   an angular separator; and
   an imager to record the image of the optical biosensor article, the first lens collimates the launch beam and concentrates the transmitted radiation from the biosensor article, the angular separator being situated before the receptacle and between the launch beam and the first lens, or after the receptacle and between the first lens and the imager.

2. The system of claim 1, further comprising at least one optical biosensor article in the receptacle.

3. The system of claim 2, wherein the plane of the virtual object image of the optical biosensor article is situated beyond the optical biosensor article and the collimating lens by from about 100 to about 200 millimeters.

4. The system of claim 1, wherein the angular separator comprises at least one transmission grating, a reflection grating, a prism, or a combination thereof.

5. The system of claim 1, further comprising a fold mirror situated between the transmission grating and the first collimating lens.

6. The system of claim 1, further comprising a second collimating lens situated between the first collimating lens and the imager.

7. The system of claim 1, further comprising at least one polarizer situated near the launch beam, near the imager, or a combination thereof.

8. The system of claim 7, wherein the at least one polarizer comprises two polarizers, and the angle between the two polarizers is other than 90 degrees.

9. The system of claim 1, wherein the launch beam comprises a super luminescent diode coupled to single-mode fiber.

10. The system of claim 1, wherein the reader has a footprint of less than about 12 inches square.

11. The system of claim 1, wherein the reader has a total volume of less than about 12 inches cubed.

12. A method for label-independent detection comprising:
providing the label-independent detection optical reader system of claim 1 an
conducting a cell-based assay or biochemical assay on the optical biosensor article, and
recording and interpreting the image.

13. The method of claim 12 wherein interpreting the image comprises comparing the location or centroid of the signal region image to the location or centroid of the reference region image for a well.

14. The method of claim 12 wherein the optical biosensor article comprises a resonant waveguide biosensor.

15. A label-independent detection system comprising:
the optical reader system of claim 1;
wherein the angular separator comprises at least one transmission grating, a reflection grating, a prism, or a combination thereof;
a fold mirror situated between the transmission grating and the first collimating lens;
a second collimating lens situated between the first collimating lens and the imager;
at least one polarizer situated near the launch beam, near the imager, or a combination thereof; and
the launch beam comprises a super luminescent diode coupled to single-mode fiber.

* * * * *